(12) United States Patent
Gugel et al.

(10) Patent No.: US 6,719,561 B2
(45) Date of Patent: Apr. 13, 2004

(54) MEDICINAL OR DENTAL HAND INSTRUMENT

(75) Inventors: Bernd Gugel, Ulm-Einsingen (DE); Hans Heckenberger, Biberach (DE); Uwe Mohn, Schelklingen (DE)

(73) Assignee: Kaltenbach & Voight, GmbH & Co.

( * ) Notice: Subject to any disclaimer, the term of this patent is extended or adjusted under 35 U.S.C. 154(b) by 122 days.

(21) Appl. No.: 10/150,421

(22) Filed: May 17, 2002

(65) Prior Publication Data

US 2002/0137006 A1 Sep. 26, 2002

Related U.S. Application Data

(62) Division of application No. 09/770,957, filed on Jan. 26, 2001, now Pat. No. 6,416,321, which is a division of application No. 09/383,776, filed on Aug. 26, 1999, now abandoned, which is a division of application No. 08/936,143, filed on Sep. 22, 1997, now abandoned.

(30) Foreign Application Priority Data

Sep. 27, 1996 (DE) ............................ 196 39 871

(51) Int. Cl.$^7$ ................................ A61C 3/02
(52) U.S. Cl. .................... 433/88; 433/80; 433/126
(58) Field of Search ............... 433/88, 80, 89, 433/90, 126, 127, 128

(56) References Cited

U.S. PATENT DOCUMENTS

| | | | | |
|---|---|---|---|---|
| 2,641,839 A | * | 6/1953 | Black | 433/80 |
| 2,696,049 A | | 12/1954 | Black | 433/88 |
| 2,814,877 A | | 12/1957 | Tilden | 433/88 |
| 3,882,638 A | | 5/1975 | Black | 451/91 |
| 4,198,755 A | * | 4/1980 | Landgraf et al. | 433/126 |
| 4,214,871 A | * | 7/1980 | Arnold | 433/216 |
| 4,403,959 A | * | 9/1983 | Hatakeyama | 433/126 |
| 4,608,018 A | | 8/1986 | Ghedini et al. | 433/88 |
| 4,648,840 A | | 3/1987 | Conger, Sr. | 433/125 |
| 4,696,645 A | | 9/1987 | Saupe et al. | 433/125 |
| 4,950,160 A | | 8/1990 | Karst | 433/88 |
| 5,125,835 A | * | 6/1992 | Young | 433/80 |
| 5,252,064 A | * | 10/1993 | Baum et al. | 433/80 |
| 2001/0031441 A1 | | 10/2001 | Ito et al. | 433/88 |

FOREIGN PATENT DOCUMENTS

| | | |
|---|---|---|
| EP | 0 0035 040 A1 | 2/1980 |
| EP | 0 035 040 A1 | 9/1981 |
| EP | 0 154 900 A1 | 2/1985 |
| EP | 0 369 043 A1 | 11/1988 |
| EP | 0 369 043 A1 | 5/1990 |
| EP | 0 154 900 A1 | 9/1995 |
| EP | 0 834 291 B1 | 9/1997 |

\* cited by examiner

*Primary Examiner*—John J. Wilson
(74) *Attorney, Agent, or Firm*—Scully, Scott, Murphy & Presser

(57) ABSTRACT

In a medicinal or dental hand instrument (1) comprising a hand piece (2) and a handle (6) arranged on the hand piece (2), an outlet opening (5), arranged on the front side of the handle (6), for the outlet of an abrasive therapeutic agent and a transport fluid, and a coupling terminal (4) for coupling the hand instrument (1) to a supply line for at least one transport fluid, in particular water and/or air, wherein the coupling terminal (4) is a coupling component (14b) of a coupling (13), the coupling component (14b) is arranged on an insert piece (20) which can be plugged into a plug-in socket or plug-in recess (19) and in its end zone, facing away from the flow, has one or more coaxially or paraxially disposed, sealed pipe socket couplings (10), which each connect a feed line (9, 11) for the transport fluid to an ongoing feed line (21, 22).

8 Claims, 2 Drawing Sheets

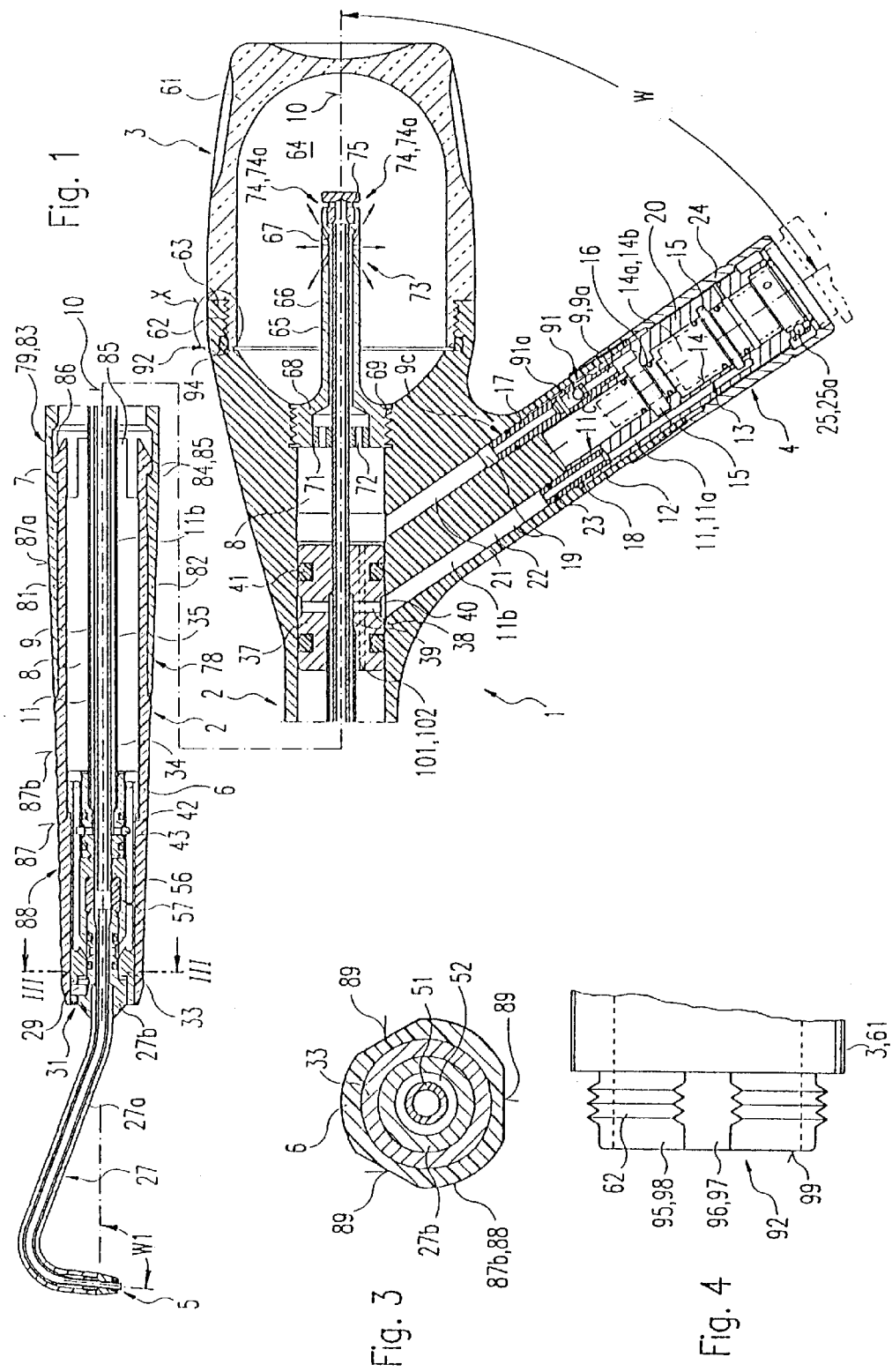

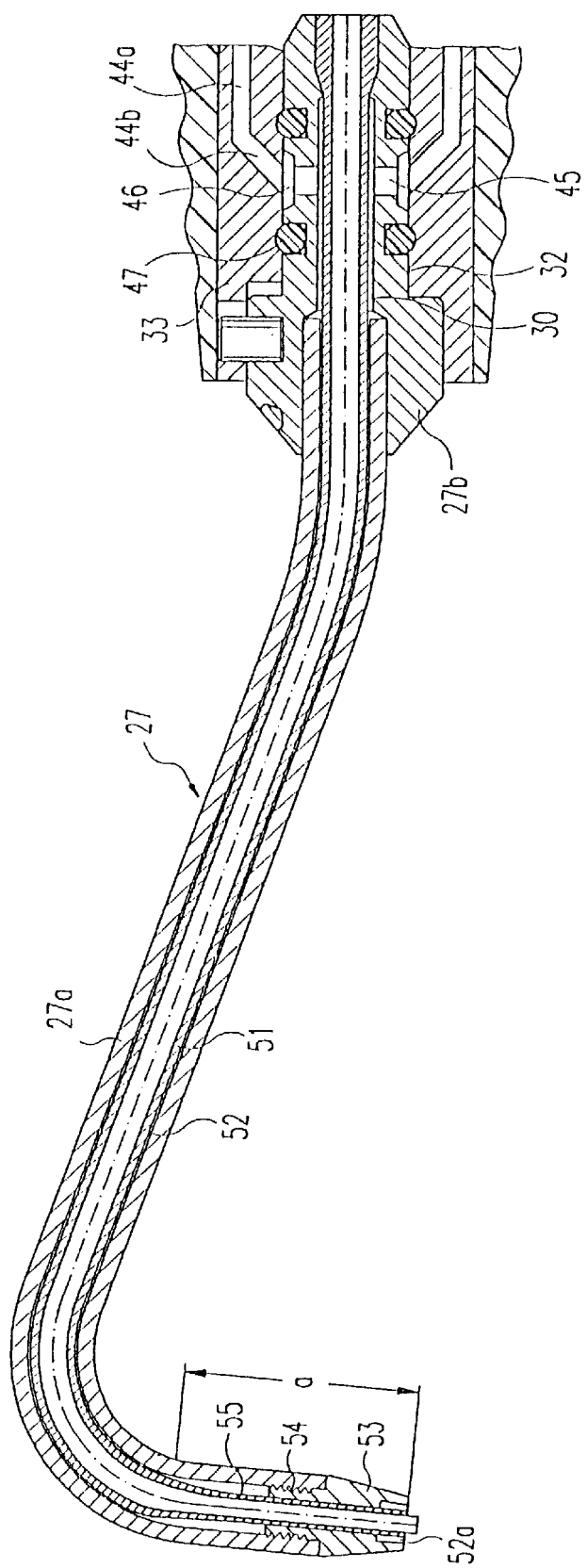

MEDICINAL OR DENTAL HAND INSTRUMENT

This application is a divisional application of Ser. No. 09/770,957, filed Jan. 26, 2001, now U.S. Pat. No. 6,416,321, which is a divisional application of Ser. No. 09/383,776, filed on Aug. 26, 1999; now abandoned which is a divisional application of Ser. No. 08/936,143; filed on Sep. 22, 1997; now abandoned.

BACKGROUND OF THE INVENTION

1. Field of the Invention

The invention relates to a medicinal or dental hand instrument which includes a handpiece and a handle arranged on the hand piece, and which incorporates a coupling element for coupling the hand instrument to a supply line for at least one transport fluid.

2. Discussion of the Prior Art

A hand instrument of this type has been described in each of publications U.S. Pat. No. 2,814,877, IT 1180538 and U.S. Pat. No. 4,648,840.

A common feature of these known hand instruments is a rod-shaped hand piece which in its front end zone has an outlet nozzle for a therapeutic agent and at its rear end has a coupling terminal for the detachable coupling of the hand piece to a flexible supply line. From the coupling terminal one or more feed lines for the therapeutic agent extend through the hand piece to the outlet terminal.

The hand piece described in U.S. Pat. No. 2,814,877 comprises a storage container for the therapeutic agent at its rear end. The coupling terminal for the supply line is arranged at the rear end of the storage container, the feed line extending coaxially through the container. The hand piece is a body permanently assembled from a plurality of longitudinal parts. In the front end zone of the hand piece a valve is arranged in the feed line, said, valve being selectively manually opened or closed by a transversely projecting actuating element. The outlet opening is situated at the front end of a hollow needle which projects from the hand piece and whose free end extends obliquely forwards relative to the longitudinal central axis of the hand instrument.

A known hand instrument somewhat comparable with the previously described known hand instrument has been described in IT 1180538. In its rear end zone this hand instrument likewise comprises a storage chamber for the therapeutic agent, a first and second centrifugal chamber for the therapeutic agent being arranged in the front half of the hand piece.

In contrast to the previously described modes of construction, a dental hand instrument described in U.S. Pat. No. 4,648,840 comprises a laterally projecting storage container which is arranged in the rear end zone of the hand instrument.

A hand instrument of the present type has to fulfil i.a. two requirements. On the one hand, it is to be easy to handle in order to be able to be moved and guided purposively and safely during use with the least possible exertion. On the other hand, a simple construction which can be manufactured cost-effectively is advisable, which in particular is of essential significance in view of the relatively small structural space available. Here it should be kept in mind that the feed line between the coupling component associated with the supply line and the coupling component associated with the hand instrument and the ongoing feed line are complex and the manufacture of these feed line sections requires a relatively large outlay in terms of production and time, with the result that the manufacturing costs are also high.

SUMMARY OF THE INVENTION

The object of the invention is, in the case of a hand instrument of the type described adapted to simplify and improve upon the coupling means for coupling to the supply line.

In this embodiment the associated coupling component and one or more coaxially or paraxially disposed, sealed pipe socket couplings are formed on a separate insert piece which can be premanufactured and assembled simply and cost-effectively. The hand piece can have a substantially simpler construction in the region of the coupling terminal. The reason for this is that the production of the feed line formed on the one hand in the separate insert piece and on the other hand in the hand instrument with the insert piece removed, thereby providing improved accessibility, is simpler and easier. This is also contributed towards by the design of the one or more pipe socket coupling(s) present between the insert piece and the hand piece, which can be produced and sealed in a simple manner and facilitate a small construction.

This embodiment according to the invention also allows the insert piece to be used as adapter for adapting the hand instrument to different coupling components associated with the supply line, when a plurality of insert pieces matching coupling components produced by different manufacturers are provided. This allows a simple adaptation of the hand instrument to different manufacturers of supply lines or devices, which adaptation can be carried out with ease of handling and both rapidly and cost-effectively.

It is a further object of the invention to design a medicinal or dental hand instrument of the type described herein so as to facilitate simpler and improved handling.

In this embodiment according to the invention, the handle, with an optionally provided hollow needle, can be rotated simply and with ease of handling independently of the rearwardly arranged shaft, and the outlet opening can be brought into selective positions. This substantially simplifies a purposive treatment of the teeth of a jaw, or of the lower- and upper jaw.

It is also advantageous to arrange the coupling terminal laterally on the hand instrument. In this way the effective lever load exerted upon the hand instrument by the flexible supply line during the handling of the hand instrument can be substantially reduced. This is due to the fact that on the one hand, on account of the lateral coupling terminal, the effective load gravity point of the flexible supply line is displaced towards the hand instrument. On the other hand, the effective distance between the coupling terminal and the handle can be substantially reduced, so that the stabilisation moment to be applied by the operator's hand during the handling of the hand instrument is also substantially reduced in this way. The advantageous outcome is that the operator can move and guide the hand instrument more simply, more easily and with less attentiveness. Consequently the operator can concentrate more upon the actual treatment with the result that an improvement in the quality of the treatment can also be achieved.

The coatings or discolourations present on body parts, in particular teeth, can be of different types and consistencies.

Therefore it is a further object of the invention to design a hand instrument of the type described in such manner that the respective body part can be purposively treated and/or the hand instrument can be adapted to the particular treatment.

In accordance with the invention, a plurality of therapeutic agents having different removing capacities can selectively be used. In this way different coatings and/or discolourations can be treated with a therapeutic agent having a greater or lesser removing capacity, on the one hand with the correct power level and on the other hand gently and thus purposively, e.g. using a therapeutic agency having a fine, medium or coarse removing capacity. Here it should be kept in mind that, in particular in the case of treatment with a coarse-acting therapeutic agent, depending upon the aggressiveness of the therapeutic agent a slight erosion of tooth substance is likely. This can be avoided or reduced to a minimum by means of the invention.

Further developments of these features of the invention facilitate a simple and easily handled adaptation of the therapeutic instrument to different therapeutic agents, and at the same time the selection of the implementation of the adaptation is simplified and facilitated.

It is a further object of the invention to protect the interior of the hand piece from contamination.

In one embodiment according to the invention, in functional operation the interior of the hand piece is subjected to excess pressure which prevents impurities and pathogenic organisms from penetrating through crevices and gaps.

It is a further object of the invention to design a hand instrument of the type described herein in such manner that contamination of the coupling is prevented.

In this embodiment an automatic closure of the feed line in the direction of the coupling takes place. In this way, in the event of an obstruction of the hand instrument, pressure relief noises and contamination upon the opening of the coupling are avoided.

It is a further object of the invention to design a hand instrument of the type described herein in such a manner that, independently of the position of the hand instrument, a substantially uniform mixture of the carrier fluid and the abrasive therapeutic agent is obtained.

This object is fulfilled by the present invention. In this embodiment the inlet opening for the transport fluid and the inner outlet opening for the mixture are situated in the central region of the accommodating chamber of the storage container. In this way these openings are situated in a region of the accommodating chamber in which, independently of the position of the hand instrument, a substantially uniform mixture quantity and concentration can discharge through the inner outlet opening. This is of considerable advantage as during the treatment the hand instrument can be held in different positions in particular in the mouth cavity of a patient, and nevertheless a substantially constant mixture is outlet from the outlet opening of the handle.

The invention further relates to an advantageous pressure relief device for the storage container which facilitates a clean opening of the storage container even when the latter is under pressure, for example in the case of an obstruction in the region of the hand instrument.

BRIEF DESCRIPTION OF THE DRAWINGS

In the following the invention and further advantages attainable by means of the invention will be explained in detail making reference to simplified drawings and advantageous exemplary embodiments. In the drawings:

FIG. 1 is a vertical longitudinal section through a medicinal, or in particular dental, hand instrument according to the invention;

FIG. 2 is a vertical longitudinal section through a hollow needle of the hand instrument;

FIG. 3 is the section III—III of FIG. 1;

FIG. 4 is a plan view of the detail referenced X in FIG. 1.

DETAILED DESCRIPTION OF PREFERRED EMBODIMENTS

The main components of the hand instrument 1 comprise a rod-shaped hand piece 2, a storage container 3 for a powdery, abrasive therapeutic agent arranged in the rear zone of the hand instrument 1, a coupling terminal 4 for the detachable coupling of the hand instrument 1 to a flexible supply line of a dentist's chair or the like, an outlet opening 5 in the front end zone of the hand instrument 1, and feed lines which extend from the coupling terminal 4 through the hand instrument 1 to the outlet opening 5.

In the present, preferred embodiment, the hand piece 2 consists of a front hand piece member, which forms a handle 6, and a rear hand piece member which forms a shaft. 7 which extends rearwardly from the handle 6 and at its rear end bears the storage container 3 and on which the coupling terminal 4 is arranged laterally.

The handle 6 and the shaft 7 are sleeve-like bodies in whose cavity 8, which preferably has a circular cross-section, one or more feed lines extend from the coupling terminal 4 to the outlet opening 5.

In the present embodiment two feed lines 9, 11 are provided, namely one for a pressure gas, in particular compressed air, and one for a therapeutic liquid, in particular water. The feed line sections 9a, 11a extending in the region of the lateral coupling terminal 4 lead into ongoing line sections—and here into the cavity 8—in the rear end zone and in a line coupling 9c, 11c forwardly offset in relation to the storage container 3. Here the feed line sections 9a, 11a preferably converge obliquely forwards into a sleeve thickened portion on which a connecting socket 12 is formed, in particular in the predetermined oblique position, which forms an acute angle W, here approximately 40° to 60°, in particular approximately 45° to 55°, with the longitudinal central axis 10 of the hand piece 2.

The hand instrument 1 is used for example to clean coatings, in particular on teeth, by means of a powdery, particle-containing flow discharged under pressure from the nozzle or outlet opening 5, as will be described further. If small hard granules, e.g. abrasive or corundum granules, are used as abrasive agent in the flow, the hand instrument is also suitable for the removal of relatively harder tissue, such as dental enamel, for example for rounding off sharp edges or adapting levels. Here, depending upon the hardness of the granules, filler materials or metals of crowns or inlays can also be removed.

The coupling terminal 4 forms part of a screw coupling or preferably a plug-in/rotary coupling 13, by means of which the coupling terminal 4 can be detachably coupled to the flexible supply line (not shown) rapidly and with ease of handling. The plug-in/rotary coupling 13 comprises a cylindrical coupling pin and a cylindrical coupling recess 14 which accommodates said pin; in the present embodiment the coupling pin (only sketched in the drawing) projects from a terminal component of the flexible supply line and the coupling recess 14 is arranged in the connecting socket 12.

The media lines extending in the flexible supply line, here for water and air, extend in the form of axially parallel channels into the region of the coupling pin 14a, passing through the hollow-cylindrical separating gap between coupling pin 14a and coupling recess 14b in a Z-formation at penetration points. At each penetration point an annular groove 15 is arranged either in the outer surface of the coupling pin 14a or in the inner surface of the coupling recess 14b, while on both sides of the penetration point a sealing ring 16 is in each case arranged in the annular groove of the coupling pin 14a or the coupling recess 14b for sealing purposes. The coupling pin 14a and coupling recess 14b can be stepped in forwardly converging fashion, as shown in FIG. 1, in which case the line connection points can be provided, axially offset, in each step.

In the present embodiment the coupling recess 14b is arranged in a cylindrical insert piece 17 which at its front end comprises for example two diametrally opposed, projecting pipe sockets 17, 18 through which the feed line sections 9a, 11a extend and which can be inserted into a corresponding plug-in recess 19 from which extend channels 21; 22 which accommodate the pipe sockets 17, 18. For sealing, annular seals 23 can be provided which are in each case arranged in annular grooves of the outer surface of the pipe sockets 17, 18 or in the inner surface of the channels 21, 22. The insert piece 20 is retained by a retaining nut 24 detachably screwed onto the connecting socket 12.

For the detachable fixing of the plug-in/rotary coupling 13, a locking device 25 is provided comprising a flexible locking element 25a which can be flexibly located in a locking recess either in the coupling pin 14a or in the coupling recess 14b and to which excess pressure can be applied in order to release the plug-in/rotary coupling 13.

In the present embodiment, the outlet opening 5 is arranged at the free end of a hollow needle 27 which extends rectilinearly or laterally obliquely or transversely and whose free end forms a right angle or obtuse angle W 1 with the longitudinal central axis 10 of the hand instrument 1. The hollow needle 27 is formed by an outer pipe 27a whose rear end is fixed to a hollow-cylindrical needle base 27b which can be detachably connected to the front end of the handle 6 by a fast-acting connection, here a bayonet connection 31. The bayonet connection 31 comprises, in a manner known per se, a locking pin, here formed by a radial pin 29 on the hollow needle base 24b, which can be introduced into a bayonet groove of the handle 6 by the insertion and rotation of the hollow needle 27 and which preferably also can be locked in a locking recess, thereby preventing it from being unintentionally turned backwards.

In the present embodiment, a plug-in recess 32 of cylindrical or stepped-cylindrical formation accommodating the hollow needle base 27b is provided in an accommodating sleeve 33 fixed in the sleeve-like handle 6, for example by pressing or gluing. In the accommodating sleeve 33 an inner pipe 34 and an outer pipe 35 are arranged in a rear, stepped bore in a stable and tightly sealed manner, the inner pipe 34 extending coaxially into the central region of the accommodating chamber 36 of the storage container 3. The outer pipe 35, which surrounds the inner pipe 34 with an annular gap, extends up to a cylindrical connecting member 37 in which a line connection is provided between the line section 9b and the annular channel between inner pipe and outer pipe 35, which channel forms an ongoing line section 11b. The connecting member is adapted to the cross-sectional dimensions of the cavity 8 and prevented from being axially displaced therein by suitable fixing measures, e.g. gluing or a locking transverse pin or a locking transverse screw. At the inlet of the line section 11a, the connecting member 37 comprises a radial connecting hole 38 which extends inwards into a front stepped hole 39 into which the rear end of the outer pipe 35 extends and is sealed therein, for example by impression. Preferably, in the transverse plane of the connecting hole 38 an annular groove 40 is provided in the outer surface of the connecting member 37 and a plurality of connecting holes 38 can also be distributed over the periphery. On both sides of the connecting hole 38 the connecting member 37 is sealed in the cavity 8 by a respective sealing ring 41 which is arranged in an associated annular groove in the outer surface of the connecting member 37 or in the inner surface of the cavity 8. The connecting member 37 can also be axially secured by being held so as to be axially undisplaceable in the accommodating sleeve 33 by means of the outer pipe 35.

In the region of the accommodating sleeve 33 the feed line 11 passes around the free end of the hollow needle base 27b. This takes place in that from a rear stepped hole 12 in the accommodating sleeve 33, which hole accommodates the outer pipe 35, one or more radial channels 43 distributed over the periphery lead(s) into a longitudinal channel 44a which extends approximately paraxially in the accommodating sleeve 33 and leads to the hollow needle base 27b and is connected to the cavity of the outer pipe 27a by a transverse channel 44b in the accommodating sleeve 33 and a transverse channel 45, connected thereto, in the hollow needle base 27b. Here again a plurality of transverse holes 45 or an associated annular groove 46 can be provided in the outer surface of the hollow needle base 27b or in the inner surface of the plug-in recess 32, annular seals 47 positioned in annular grooves in the hollow needle base 47b or in the accommodating sleeve 33 being arranged on both sides.

The outer pipe 27a of the hollow needle 27 contains an inner pipe 51 whose outer cross-sectional dimensions are smaller than the inner cross-sectional dimensions of the outer pipe 27a, so that a gap 52 exists between the latter and the inner pipe 51. When the inner pipe 51 extends coaxially in the outer pipe 27a, this gap 52 is an annular gap. This is not necessary however, as the inner pipe 51 can bear against the outer pipe 27a on one side. The inner pipe 51 extends into the free end zone of the outer pipe 27a and can terminate with the latter or be set back or forwards somewhat in relation to the latter, as shown. In the present embodiment the free end zone of the inner pipe 51 is held in a preferably convergent cap 53 which is screwed to the facing end of the outer pipe 27a, in particular is screwed-in with a thread attachment 54.

The cap 53 surrounds the inner pipe 51 at a distance comparable with the small gap 52. To homogenise the outflow, it is advantageous to form a gap enlargement 52a at the free end of the gap 52.

It is advantageous to taper the cross-section of the threaded pipe 51 at a distance a before its free end. In this way the cross-section of the inner pipe 51 is reduced in size and the flow- and outlet speed of the through-flowing medium, here water, is increased, thereby contributing towards the efficiency of the abrasive treatment and also improving the mixing of the media with the abrasive agent. The cross-sectional tapering 55 is preferably not to be stepped but gradual or conical in order to avoid an edge likely to result in obstructions. In the remainder of the inner pipe 51, its inner cross-section is somewhat larger, whereby the risk of obstruction is reduced. In the present embodiment, the distance a amounts to approximately 5 to 10 mm.

The gap 52 continues in the region of the hollow needle base 27b to the rear of the transverse hole 45, while a longitudinal hole 30 accommodating the outer pipe 27a has corresponding dimensions, being optionally stepped. The rear end of the inner pipe 51 is tightly connected to the rear end of the hollow needle base 27b, for example is impressed therein or soldered thereto, when the hollow needle base 27b and inner pipe 51 consist of metal. In the present embodiment the rear end of the inner pipe 51 is somewhat thickened in its end region and impressed into the longitudinal hole 30 or a stepped enlargement thereof, thereby ensuring sealing tightness.

To seal the rear end of the hollow needle base 27b and the front end of the inner pipe 34, a preferably sleeve-like sealing ring 56 is provided which is positioned in the base of the plug-in recess 32, the front end of the inner pipe 34 preferably projecting into the hole of the sealing ring 45 which is adapted to the outer cross-section of the inner pipe 34. The length of the sealing ring 56 is made somewhat larger than the distance between the inner pipes 34 and 51 or between the inner pipe 34 and the hollow needle base 27b. Consequently the sealing ring 56 is axially compressed upon the mounting of the hollow needle 27, here with the bayonet connection, with the result that the sealing tightness of this sealing device, bearing the general reference 57, is ensured. The sealing ring 56 therefore consists of elastically compressible material, such as rubber or plastics for example.

The storage container 3 forms the rear end of the hand instrument 1, being arranged coaxially with the hand piece 2 and having a hat-like cover 61 which can be screwed to a flat or ring-shaped container base 63 by a screw thread 62 disposed in its free edge zone. Preferably the container base 63 is cup-shaped, whereby the accommodating chamber. 64 of the storage container 3 is enlarged. The cover 61 preferably consists of transparent material, e.g. glass, quartz or plastics.

The inner pipe 34 passes through the connecting member 37 in the stepped hole 39, being accommodated in the rear section of the stepped hole 39 in tightly sealed fashion. That part of the cavity 8 situated behind the connecting member 37 is closed off from the accommodating chamber 64 by a sleeve 65 which surrounds the inner pipe 34 with an annular gap 66, the inner pipe 34 extending up to or into an inner shoulder 67 in the rear end zone of the sleeve 65. The annular gap 66 represents a rearwardly directed extension of the cavity 8. The sleeve 65 is inserted or screwed into the hole formed by the cavity 8 in tightly sealed fashion. In the present embodiment the cross-section of the sleeve 65 is made smaller than the cross-section of the cavity 8, and the sleeve 65 has a flange 68 with an outer thread 69 which is screwed into an inner thread of the cavity 8. The flange 68 itself, or a support ring 71 inserted therein, holds the rear end zone of the inner pipe 37 in the axial position. The support ring 71 comprises a longitudinally directed perforation or through-holes 72 to ensure the passage of air into the annular gap 66. In a preferably central position relative to the accommodating chamber 64, the sleeve 65 contains a plurality of transverse holes 73 which connect the annular gap 66 to the accommodating chamber 64. In the longitudinal direction of the central axis 10 are arranged a plurality of—here in each case three—transverse holes 73, of which the or a central hole extends approximately radially and the or a front hole and the or a rear hole diverge obliquely outwards. The transverse holes 73 can also be distributed over the periphery.

At its free end positioned approximately in the central zone of the accommodating chamber 64, the sleeve 65 has at least one axial inlet hole 74 which is arranged coaxially with the free inner cross-section of the inner pipe 34. In the present embodiment the inlet hole 74 is preceded by a disc 75 which forms radial access holes 74a. In the present embodiment the disc forms part of a nut which is screwed into a corresponding threaded recess at the rear end of the sleeve 65.

The handle 6 and the shaft 7 are mounted together in a pivot bearing 78 so as to be rotatable in relation to one another about the longitudinal central axis 10, at the same time being held axially together by a connecting device 79. The pivot bearing 78 is formed by a suitable over-engagement of the sleeve bodies of handle 6 and shaft 7. In the present embodiment the handle 6 comprises a sleeve attachment 81 which projects coaxially from its rear end and is preferably tapered and is surrounded by a projecting sleeve casing 82 of the shaft 7 with a small movement play. The connecting device 79 is formed by a locking device 83 with at least one radial, outwardly directed locking nose 84 on a locking arm 85 rearwardly projecting from the sleeve attachment 81, where the locking nose 84 engages behind a locking edge on the inside of the sleeve attachment 82. On the rear the locking arm 85 has a convergent lead-in surface 86 which upon insertion causes the elastic locking arms 85 to bend inwards automatically. The sleeve attachment 82 preferably converges forwards and is provided with a conical outer surface 87a, merging into the outer surface 87 of the handle 6 in an approximately closing manner. To improve the stability of grip, the outer surface 87 is provided with a grip structure. In the present embodiment, alternating annular shafts 88 and annular recesses are provided in the longitudinal direction, these preferably being rounded and merging into one another at only slightly inclined annular flank surfaces. To further improve the stability of grip, the outer surface 87b comprises three grip surfaces 89 uniformly distributed over the periphery which permit an advantageous three-point holding of the handle 6 between three fingers of the operator's hand, while the shaft 7 can rest on the central region of the hand, in particular between the index finger and the thumb. The bearing point in the shaft 7 is situated in the vicinity of the connecting socket 12.

The rotatability of the handle 6 allows the position of the hollow needle 27 to be adapted to the respective treatment location. For its rotation, the handle 6 merely requires to be rotated by the fingers by which it is gripped, with co-rotation of the hollow needle 27. The shaft 7 now rests on the base area between the index finger and the thumb of the back of the hand. Due to the weight of the flexible supply line, the shaft 7 can remain in its respective rotary position upon the rotation of the handle 6.

In functional operation the therapeutic liquid in the feed line 11 and the compressed air in the feed line 9 can simultaneously flow through the rotary/plug-in coupling into the hand piece 2, where the compressed air firstly flows rearwards through the annular gap 66 and out of the transverse holes 72, preferably in distributed fashion, into the accommodating chamber 64 and centrifuges the abrasive agent contained therein, e.g. sodium bicarbonate or potassium sulphate in powder form. The resultant air/powder mixture flows through the inlet hole 74 or, if a disc 75 is provided, through the access holes 74a and the inlet hole 74 into the inner sleeve 34 and on to the outlet opening 5, where it is mixed with the water and forms an abrasive flow for the removal of coatings from teeth and the like. The previously described supply of the media can be triggered by a suitable switch. In the present embodiment a foot-operated switch is provided which electrically actuates corresponding opening valves of a control device for the media.

To prevent the abrasive material from passing into the region of the plug-in/rotary coupling 13, in the feed line section 9a there is arranged a non-return valve 91 whose valve body, preferably a valve ball, blocks a backwards flow in the feed line section 11a. In this way, other hand instruments 1, e.g. turbines, which can likewise be coupled by the plug-in/rotary coupling 13, are protected from contamination and damage by the abrasive agent.

Without the previously described blocking means, the abrasive material could enter the region of the plug-in/rotary coupling 13, for example by virtue of its own weight, after the switching off of the hand instrument 1 or in the event of the following malfunction.

In the event of an obstruction in the air/powder mixture feed line, e.g. in the region of the hollow needle 27, the arising air pressure builds up in the cavities of the hand instrument 1 traversed by the compressed air. In this pressure state it is unfavourable to open the plug-in/rotary coupling 13 or the storage container 3 since upon opening, the accumulated pressure present in the cavities of the hand instrument 1 is discharged, which is particularly unfavourable in the case of the storage container 8 since powder particles are entrained with the discharge, which is undesirable.

Preferably the non-return valve 91 is arranged in the region of the base of a front-end stepped bore 91a into which a sleeve, in each case forming the pipe sockets 17, 18, is in each case permanently inserted at a distance from the step which accommodates the non-return valve 91.

The storage container 3 comprises a special pressure relief device 92 which ensures the relief of pressure before the storage container 3 is opened, here before the cover 61 is removed. In the sealing surface 95 which cooperates with the sealing ring 94, the pressure relief device 92 contains a recess 96 which, upon the unscrewing of the cover 61, forms a small passage for the pressurized compressed air through which the latter can be discharged before the cover is disengaged from the threading. Hardly any powder escapes during this pressure relief, in particular when the cover 61 is opened with the hand instrument in a position in which the thus formed outlet opening faces upwards and the powder is present on the base of the cover. In the present embodiment the recess is formed by one or more flattened portions 97 distributed over the periphery which are arranged on the circular outer surface 98 of an annular attachment 99 which comprises the outer thread and which in its free edge zone cooperates with the sealing ring 94. The at least one flattened portion 97 only requires to be arranged in the free edge zone of the annular attachment. However, it can also extend over the entire length of the annular attachment 99, in which case the thread is likewise flattened.

The abrasive agent consists of a material which dissolves in moisture or water and thus can be flushed relatively easily out of the treatment location, here the mouth cavity of the patient. To improve the taste it is advantageous to admix a pleasant flavouring, e.g. lemon or orange flavouring, to the abrasive agent or powder.

A powder with a granule size of between approximately 15 $\mu$m and 125 $\mu$m is particularly suitable for the removal and cleaning of coatings on teeth.

As the coating or soiling or discolouration on the teeth can differ in thickness or consistency, it is advantageous to assign a plurality of types of powder having different removal capacities and abrasive power to the hand instrument 1, in each case in a storage container. It is also advantageous to make available powders in a plurality of different granule sizes or ranges, such as coarse, medium and fine, or coarse and fine, in storage containers. In the latter case for example the powder for coarse work can have a granule size of 60 $\mu$m to 100 $\mu$m while the powder for fine work can have a granule size of between 15 $\mu$m and 50 $\mu$m. The latter granule size is suitable both for fine work on sensitive teeth and also for the polishing of teeth.

It is also advantageous to assign to the hand instrument 1 a plurality of hollow needles 27 or hollow needle heads 53, all of which are suitable for mounting on the hand piece 2 or the hollow needle 27 respectively but which differ in respect of their shape and/or size or in respect of the size of their outlet opening 5. By selecting and replacing a specific one of different hollow needles 27 or hollow needle caps or heads 53 of different shapes and/or sizes, the hand instrument can also be adapted to difficult treatment locations. By selecting different sized hollow needles 27 or different sized outlet openings 5 it is possible to influence the effectiveness of the therapeutic flow issuing from the outlet opening 5 and thus to define the power level for the purposive execution of coarse or more fine work. Additionally, hollow needles 27 with a different size of outlet opening 5 are suitable for powders with different granule sizes or different removing capacities.

In order to be able to differentiate between different types of powders, it is advantageous to produce the powder types in different colours. If a plurality of different hollow needles 27 or hollow needle heads 53 assigned to specific types of powders are provided, it is advantageous for the hollow needles or hollow needle heads to be provided with a corresponding mark which indicates the association of the matching powder. Preferably this mark is a coloured mark of the same colour as the associated powder.

It is also advantageous to assign to the hand instrument 1 a plurality of different sized outlet- and/or inlet nozzles, here formed by the at least one outlet hole 73 and/or inlet hole 74, for the carrier air flow and/or for the mixture of air and abrasive agent, which can be interchanged in accordance with the desired granule size of the powder. Here preferably a set of parts comprising a hollow needle 27 and an outlet- and/or inlet nozzle, here the sleeve-shaped nozzle carrier 15, can be adapted to one another in respect of the through-openings.

In the present exemplary embodiment the insert piece 20, the hollow needle 21, the accommodating sleeve 33, the connecting member 37, the inner pipe and outer pipe 34, 35, the sleeve 65, and optionally also the disc 75, are composed of in particular hard metal, preferably steel, thereby avoiding premature wear of these parts. The handle 6 and/or shaft 7 and/or cover 61 and storage container 3 consist of metal, plastics material or preferably glass. These materials can also be produced simply and cost-effectively even in the case of a difficult construction and are insensitive to disinfectant- and sterilising agents. Also, no electrostatic charge exists, in particular in the case of glass.

In the operation of a hand instrument 1 of the type in question, the risk exists that moisture and/or abrasive material may penetrate through small crevices and gaps in the front region of the hand piece 2 into the interior of the hand piece, where they can contaminate and damage for example the connecting device 31 for the hollow needle 27 and/or the pivot bearing 78. To avoid this, the interior 8 of the hand piece 2 is connected by a line connection 101 to the feed line 9 for the compressed air. The air pressure can thus propagate into the interior, optionally also escaping from the crevices or gaps, and prevent the penetration of the aforementioned contaminating material. In the present embodiment, the rearwardly extending feed line section, namely the rear part of the interior 8, is connected to the front part of the interior 8 by a through-hole 102 in the connecting member 37. In this way, by virtue of the inner pressure, no contaminating material can penetrate either into the crevices of the pivot bearing 78 or in the region of the connecting device 31.

It is advantageous to admix fluorine or a fluorine-containing medium, in particular likewise in powder form, to the abrasive powdery agent. This ensures that during the treatment fluorine penetrates into the tooth surface, hardening and stabilising the latter. Due to the flow speed and resultant impact of the fluorine-containing particles, the influence on the tooth surface is particularly effective.

What is claimed is:

1. A medical or dental hand instrument (1), comprising: a handpiece (2), a grip part (6) being arranged on the handpiece (2), a cannula (27) located at the front end of the grip part (6), said cannula having an outlet opening (5) at a front end of the cannula (27) for the discharge of an abrasive treatment medium and of a transport fluid, a shaft (7) extending rearwardly from the grip part (6), a supply container (3) for the abrasive treatment medium being arranged on the shaft (7), a coupling connection (4) for coupling said hand instrument (1) with a feed line for at lest one said transport fluid, said grip part (6) and said shaft (7) being mounted on each other so as to be freely rotatable about a longitudinal center axis (10), and wherein said coupling connection (4) comprises a coupling element of a plug-in/rotary coupling (13).

2. A hand instrument according to claim 1, wherein a quick-action connector couples said cannula (27) with the grip part (6).

3. A medical or dental hand instrument (1) for spraying an abrasive treatment medium, comprising a handpiece (2), a supply container (3) for the abrasive treatment medium, communicating with said handpiece, a coupling connection (4) for a transport fluid, a rotatable and detachable cannula (27) having an outlet opening (5) for the abrasive treatment medium and the transport fluid, a quick-acting connection for releasably connecting the cannula (27) with the handpiece, said handpiece (2) having in a forward region thereof a grip part (6) for holding the cannula (27), a shaft (7) extending rearwardly from said grip part, and wherein the grip part (6) and the shaft (7) are mounted on each other so as to be freely rotatably relative to each other about a longitudinal center axis (10).

4. A hand instrument according to claim 2 or 3, a bayonet connection (130) couples said cannula (27) with the grip part (6).

5. A hand instrument according to claim 3, wherein the coupling connection (4) comprises a coupling part with a plug-in/rotary coupling (13).

6. A hand instrument according to claim 1 or 3 wherein said grip part (6) includes a rear sleeve part (81) and the shaft (7) includes a front sleeve part (82), said sleeve parts (81, 82) engaging coaxially each other at a slight play facilitating relative movement therebetween, with the sleeve part (82) of the shaft (7) engaging over the sleeve part (81) of the grip part (6).

7. A hand instrument according to claim 3, wherein the quick-acting connection (31) connect the cannula (27) with a front end of the grip part (6).

8. A hand instrument according to claim 1 or 3, wherein latching means (83) connect the grip part (6) and the shaft (7) with other.

* * * * *